(12) United States Patent
Teverovskiy et al.

(10) Patent No.: US 10,934,281 B2
(45) Date of Patent: Mar. 2, 2021

(54) NITROGEN AND DIOXOLANE-CONTAINING HYDROFLUOROETHERS AND METHODS OF USING THE SAME

(71) Applicant: 3M INNOVATIVE PROPERTIES COMPANY, St. Paul, MN (US)

(72) Inventors: Georgiy Teverovskiy, St. Louis Park, MN (US); Michael G. Costello, Afton, MN (US); William M. Lamanna, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 10 days.

(21) Appl. No.: 16/323,282

(22) PCT Filed: Aug. 22, 2017

(86) PCT No.: PCT/US2017/047879
§ 371 (c)(1),
(2) Date: Feb. 5, 2019

(87) PCT Pub. No.: WO2018/044613
PCT Pub. Date: Mar. 8, 2018

(65) Prior Publication Data
US 2020/0190071 A1 Jun. 18, 2020

Related U.S. Application Data

(60) Provisional application No. 62/380,617, filed on Aug. 29, 2016.

(51) Int. Cl.
*C07D 413/06* (2006.01)
*C07D 317/28* (2006.01)
*C07D 405/06* (2006.01)
*C09K 5/10* (2006.01)

(52) U.S. Cl.
CPC ......... *C07D 413/06* (2013.01); *C07D 317/28* (2013.01); *C07D 405/06* (2013.01); *C09K 5/10* (2013.01)

(58) Field of Classification Search
CPC ... C07D 413/06; C07D 317/28; C07D 405/06
See application file for complete search history.

(56) References Cited

U.S. PATENT DOCUMENTS

| 4,985,556 A | 1/1991 | Abe |
| 5,104,034 A | 4/1992 | Hansen |
| 2010/0139274 A1 | 6/2010 | Zyhowski |

FOREIGN PATENT DOCUMENTS

| JP | 01070445 | 3/1989 |
| WO | WO 2016-011220 | 1/2016 |
| WO | WO 2016-048808 | 3/2016 |

OTHER PUBLICATIONS

ASTM D-3278-96 e-1, "Standard Test Method for Flash Point of Liquids by Small Scale Closed-Cup Apparatus", Oct. 1997.
Ellis, "Cleaning and contamination of electronics components and assemblies" Electrochemical Publications Limited, 1986, Scotland, pp. 182-196.
Moldavskii, "Polyfluorinated organic compounds. IV. Reaction of Polyhydric alcohols with some internal perfluoroolefins", Russian jounal of general chemistry, 1996, vol. 66, No. 12, pp. 1939-1946.
Snegirev, "Reacion of perfluoro-2-methyl-2-pentene with bifunctional nucleophiles", Plenum publishing corporation, 1986, pp. 1906-1915.
International Search report for PCT International Application No. PCT/US2017/047879 dated Jan. 18, 2018, 5 pages.

*Primary Examiner* — Rebecca L Anderson
(74) *Attorney, Agent, or Firm* — Julie Lapos-Kuchar

(57) ABSTRACT

Described herein is dioxolane-containing compound of formula (I) wherein (i) $Rf^1$ and $Rf^2$ are independently linear or branched perfluoroalkyi groups having with 1-8 carbon atoms and optionally comprise at least one catenated heteroatom, or (ii) $Rf^1$ and $Rf^2$ are bonded together to form a ring structure having 4-6 carbon atoms and optionally comprise one or more catenated heteroatoms; $Rf^2$ is a linear or branched perfluoroalkyi groups having with 1-3 carbon atoms; and $R^4$ and $R^5$ are independently selected from H, F, Cl, a linear or branched alkyl group having 1-3 carbon atoms, optionally wherein the alkyl group comprises at least one of: fluorine, chlorine, a hydroxyl group, or a catenated heteroatom; for use in cleaning compositions, as an electrolyte solvent, as a heat transfer fluid, or a vapor phase soldering fluid. There is also provided a method of making the dioxolane-containing compound, comprising: contacting a 1,2-diol compound with a fluorinated ethylenically unsaturated compound in the presence of a base.

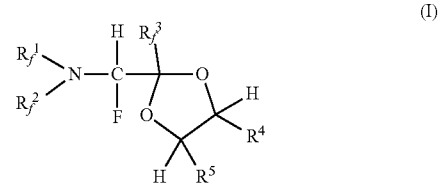

18 Claims, No Drawings

NITROGEN AND DIOXOLANE-CONTAINING HYDROFLUOROETHERS AND METHODS OF USING THE SAME

CROSS REFERENCE TO RELATED APPLICATIONS

This application is a national stage filing under 35 U.S.C. 371 of PCT/US2017/047879, filed Aug. 22, 2017, which claims the benefit of U.S. Application No. 62/380,617, filed Aug. 29, 2016.

TECHNICAL FIELD

The present disclosure relates to hydrofluoroethers containing dioxolane and amine moieties, and methods of using the same.

SUMMARY

There continues to be a need for inert fluorinated fluids which have low global warming potential while providing high thermal stability, low toxicity, nonflammability, good solvency, and a wide operating temperature range to meet the requirements of various applications. Those applications include, but are not restricted to, heat transfer, solvent cleaning, fire extinguishing agents, and electrolyte solvents and additives.

In one aspect, a dioxolane-containing compound of formula (I) is described:

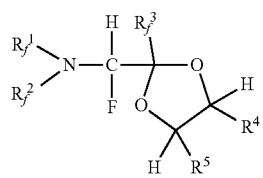

wherein (i) $R_f^1$ and $R_f^2$ are independently linear or branched perfluoroalkyl groups having with 1-8 carbon atoms and optionally comprise at least one catenated heteroatom, or (ii) $R_f^1$ and $R_f^2$ are bonded together to form a ring structure having 4-6 carbon atoms and optionally comprise one or more catenated heteroatoms;

$R_f^3$ is a linear or branched perfluoroalkyl groups having with 1-3 carbon atoms; and $R^4$ and $R^5$ are independently selected from H, F, Cl, a linear or branched alkyl group having 1-3 carbon atoms, optionally wherein the alkyl group comprises at least one of: fluorine, chlorine, a hydroxyl group, or a catenated heteroatom.

In one aspect, a working fluid is described comprising the dioxolane-containing compound of formula (I) described above.

In another aspect, an apparatus for heat transfer is described comprising the dioxolane-containing compound of formula (I) described above, The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B);

"alkyl" refers to a monovalent group that is a radical of an alkane, which is a saturated hydrocarbon. The alkyl group can be linear, branched, cyclic or combinations thereof;

"catenated" means an atom other than carbon (for example, oxygen or nitrogen) that is bonded to at least two carbon atoms in a carbon chain (linear or branched or within a ring) so as to form a carbon-heteroatom-carbon linkage; and "perfluorinated" means a group or a compound wherein all hydrogen atoms in the C—H bonds have been replaced by C—F bonds.

As used herein, a chemical structure that depicts the letter "F" in the center of a ring indicates that all unmarked bonds of the ring are fluorine atoms.

It should be understood, that although not shown, there are hydrogen atoms bonded to the carbon atoms of the cyclic ring to complete the valency of the individual carbon atoms, as is common nomenclature.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

WO Publ. No. 2016/048808 (Lamanna et al.) describes nitrogen-containing hydrofluoroether compounds which can be used in a variety of applications. WO Publ. No. 2016/048808 describes a method of making such compounds, wherein the additional of a diol to a perfluorinated vinyl amine (i.e., N(Rf$_1$)(Rf$_2$)-CF=CF$_2$) in the presence of a base results in the dimerization of the perfluorinated vinyl amine as shown in Examples 10, 16, 18, 25-27 and 30. Surprisingly, in the present disclosure it has been discovered that by reacting a 1,2-diol with a perfluorinated 1-alkyl amine in the presence of a base results, not in a dimerization of the amine compound, but instead a dioxolane-containing amine compound as illustrated in Scheme 1.

Scheme 1

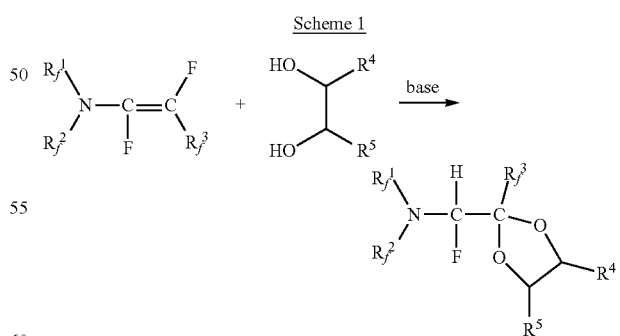

In one embodiment, the compounds of the present disclosure can be readily prepared in high yield via low cost starting materials. The starting materials can be readily purchased or derived from electrochemical fluorination. Thus, the compounds described in the present disclosure represent a new class of useful and potentially low cost fluorinated fluids that offer potential advantages in a variety of applications including heat transfer, cleaning, and electrolyte applications.

The dioxolane-containing compounds of the present disclosure (herein referred to interchangeably as a compound of the present disclosure) are of the general formula (I)

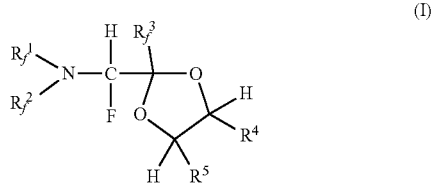

wherein (i) $R_f^1$ and $R_f^2$ are independently linear or branched perfluoroalkyl groups having with 1-8 carbon atoms and optionally comprise at least one catenated heteroatom such as an O, N, or S, or (ii) $R_f^1$ and $R_f^2$ are bonded together to form a fluorinated ring structure having 4-6 carbon atoms and optionally comprise one or more catenated heteroatoms; $R_f^3$ is a linear or branched perfluoroalkyl groups having 1-3 carbon atoms; and $R^4$ and $R^5$ are independently selected from H, F, Cl, and a linear or branched alkyl group having 1-3 carbon atoms, optionally wherein the alkyl group comprises at least one of: fluorine, chlorine, a hydroxyl group, or a catenated heteroatom.

Exemplary $R_f^1$ and $R_f^2$ groups include: $-CF_3$, $-C_2F_5$, $-C_3F_7$, $-CF_2OCF_3$, $-CF_2OCF_3$, and $-CF_2OCF(CF_3)_2$.

In one embodiment, $R_f^1$ and $R_f^2$ are bonded together to form a 5, 6, or 7 membered ring structure. In one embodiment, $R_f^1$ and $R_f^2$ are bonded together to form a 6-membered ring comprising a catenated O atom, forming for example a fluorinated morpholine ring. In another embodiment, $R_f^1$ and $R_f^2$ are bonded together in a ring structure comprising an additional catenated nitrogen atom, wherein said additional nitrogen heteroatom is tertiary and is bonded to a perfluoroalkyl group having 1-3 carbon atoms. In one embodiment, $R_f^1$ and $R_f^2$ are bonded together to form a 6-membered ring comprising an additional catenated nitrogen atom, forming for example a fluorinated piperazine ring, wherein said additional nitrogen heteroatom is tertiary and is bonded to a perfluoroalkyl group having 1-3 carbon atoms. In one embodiment, $R_f^1$ and $R_f^2$ are bonded together to form a pyrrolidine group.

Exemplary $R_f^3$ groups include $CF_3$, $CF_2CF_3$, $CF(CF_3)_2$, and $(CF_2)_2CF_3$.

In one embodiment, $R^4$ and $R^5$ are both H.

Exemplary dioxolane-containing compound of the present disclosure include:

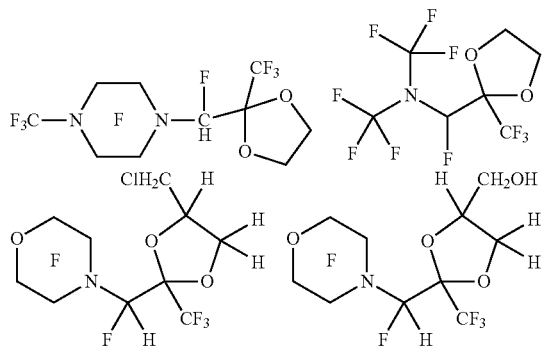

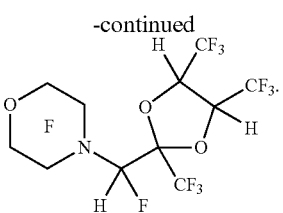

In some embodiments, the dioxolane-containing compounds of the present disclosure may exhibit properties that render them particularly useful as heat transfer fluids for the electronics industry. For example, the dioxolane-containing compound may be chemically inert (i.e., they do not easily react with base, acid, water, etc.), and may have high boiling points (up to 300° C.), low freezing points, low viscosity, high thermal stability, good thermal conductivity, adequate solvency for a range of potentially important solutes, and low toxicity.

The compounds of the present disclosure have good environmental properties as well as having good performance attributes, such as non-flammability, chemical inertness, high thermal stability, good solvency, etc.

In one embodiment, the compound of the present disclosure may have a low environmental impact. In this regard, the compounds of the present disclosure may have a global warming potential (GWP) of less than 100, 50, 40, or even 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In one embodiment, the compounds of the present disclosure have atmospheric lifetime of less than 1 year, 0.75 years, 0.05 years, or even less than 0.1 years.

Non-flammability can be assessed by using standard methods such as ASTM D-3278-96 e-1, D56-05 "Standard Test Method for Flash Point of Liquids by Small Scale Closed-Cup Apparatus". In one embodiment, the compound of the present disclosure is non-flammable based on closed-cup flashpoint testing following ASTM D-327-96 e-1.

In one embodiment, the compound of the present disclosure is non-bioaccumulative in animal tissues. For example, some compounds of the present disclosure may provide low log $K_{ow}$ values, indicating a reduced tendency to bioaccumulate in animal tissues, where $K_{ow}$ is the octanol/water partition coefficient, which is defined as the ratio of the given compound's concentration in a two-phase system comprising an octanol phase and an aqueous phase. In one embodiment, the log $K_{ow}$ value is less than 6, 5, or even 4.

In one embodiment, the compound of the present disclosure is expected to provide low acute toxicity based on 4 hour acute inhalation or oral toxicity studies in rats following U.S. EPA "Health Effects Test Guidelines OPPTS 870.1100 Acute Oral Toxicity" and/or OECD Test No. 436 "Acute Inhalation Toxicity-Acute Toxic Class Method". For example, a compound of the present disclosure has a single dose oral median lethal dose (LD 50) in male and female Sprague-Dawley rats of greater than 30, 50, 100, 200, or even 300 mg/kg.

The useful liquid range of a compound of the present disclosure is between its pour point and its boiling point. A pour point is the lowest temperature at which the compound is still able to be poured. The pour point can be determined, for example, by ASTM D 97-16 "Standard Test Method for Pour Point of Petroleum Products". In one embodiment, the compound of the present disclosure has a pour point of less than 0° C., −20° C., −40° C. or even −60° C. In one embodiment, the compound of the present disclosure has a boiling point of at least 100° C., 150° C., 200° C., 250° C. or even 300° C.

In some embodiments, the compound of the present disclosure may be hydrophobic, relatively chemically unreactive, and thermally stable.

As mentioned above, the compound of the present disclosure may be prepared by a nucleophilic addition of a 1,2-diol with an ethylenically unsaturated compound in the presence of a suitable base to form a dioxolane ring. The ethylenically unsaturated compound comprises an internal double bond alpha to an amine and at least one olefinic C—F bond. In one embodiment, the ethylenically unsaturated compound is perfluorinated.

The ethylenically unsaturated fluorinated compound can be prepared by standard synthetic procedures that are well known in the art, including those described by Abe in JP 01070444A and JP 0107445A, which are incorporated herein by reference.

Representative examples of ethylenically unsaturated fluorinated compound useful as starting compounds for preparing the dioxolane-containing hydrofluoroethers of this disclosure include, for example, 1-propenyl amines, shown in FIG. 1. Although the structures in FIG. 1 are all shown as trans isomers, the corresponding cis isomers are equally useful starting compounds. Typically the cis and trans ethylenically unsaturated fluorinated compounds of FIG. 1 are made and used as a mixture of cis and trans isomers.

FIG. 1: Perfluorinated 1-Propenyl Amines

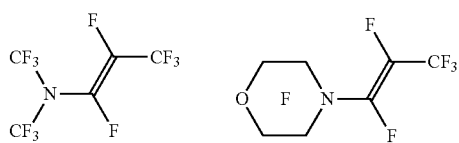

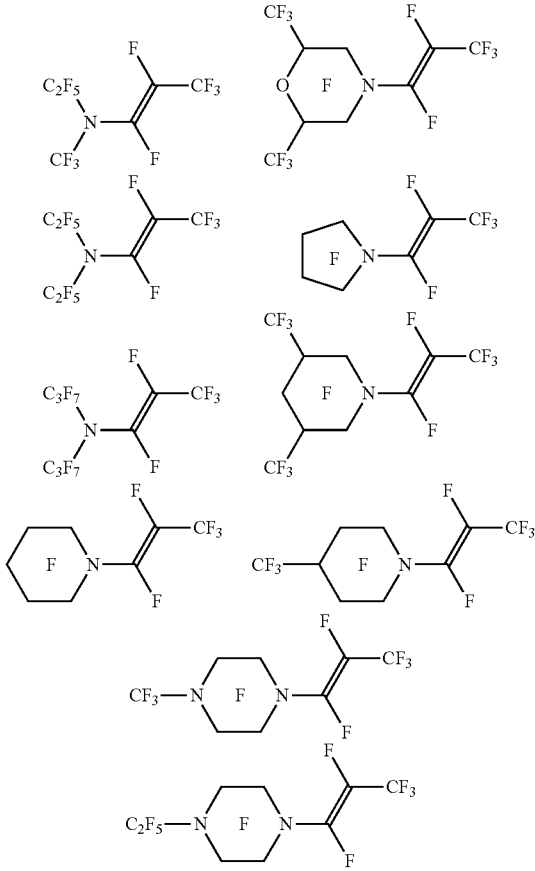

Note: The 1-propenyl amines in FIG. 1, above, can be cis or trans isomers or a mixture thereof, although only the trans isomers are shown.

Useful 1,2-diols are generally commercially available or readily prepared and provide useful starting compounds for preparing the dioxolane-containing hydrofluoroether compositions of this disclosure in high yield. In some embodiments, hydrocarbon diols may be employed due to their relatively lower cost (in comparison with fluorocarbon diols). In some embodiments, suitable alcohols are generally those that provide dioxolane-containing compounds of the present disclosure that are non-flammable.

Representative examples of suitable 1,2-diols include, for example, ethylene glycol, propane-1,2-diol, butane-1,2-diol, 3-chloropropane-1,2-diol, 3-fluoropropane-1,2-diol, glycerol, etc.

In one embodiment, the ratio of the ethylenically unsaturated fluorinated compound to the 1,2-diol is 1:2 to 2:1 with 1:1 typically used. The alcohol addition reaction illustrated in Scheme 1 can be effected by combining the ethylenically unsaturated compound and the 1,2-diol in the presence of at least one base (for example, a Lewis base). Useful bases include potassium carbonate, cesium carbonate, potassium fluoride, potassium hydroxide, potassium methoxide, triethylamine, trimethylamine, potassium cyanate, potassium bicarbonate, sodium carbonate, sodium bicarbonate, sodium methoxide, cesium fluoride, lithium t-butoxide, potassium t-butoxide, and the like, and mixtures thereof; with potassium carbonate, potassium hydroxide, and mixtures thereof being preferred. A metal salt of the starting 1,2-diol reagent can also be used as the base. Typically the base is present at about 2 to 3 equivalents based on the ethylenically unsaturated fluorinated compound.

The reactants and base can be combined in a reactor (for example, a glass reactor or a metal pressure reactor) in any order, and the reaction can be run at a desired temperature with agitation. Generally, however, use of a non-reactive, aprotic organic solvent (for example, acetonitrile, acetone, tetrahydrofuran, glyme, or a mixture of two or more thereof) can facilitate the reaction.

In one embodiment, the run temperature is from about 0° C. to about 80° C. Generally, the run temperature is above the boiling point of the ethylenically unsaturated compound.

The reaction can occur at ambient or higher pressures (e.g., >760 Torr). In one embodiment the reaction is conducted in a sealed pressure vessel. In one embodiment, the reaction is exothermic so cooling of the reaction vessel can be used to maintain reaction pressure.

The reaction is run to completion (e.g., 12 hours). The reaction produces a dioxolane-containing compound, which is typically a mixture of various isomers.

The product can then be washed with water to remove base, salts and residual alcohol. The recovered water layer can be washed with low boiling nonfunctional fluorochemical to collect the fluorinated product and maximize yield. The low boiling nonfunctional fluorochemical can then be subsequently removed to isolate the fluorinated product. In one embodiment, the reaction yields are greater than 50, 60, 70 or even 75%. Exemplary low boiling nonfunctional fluorochemicals include those available under the trade designation "3M PERFORMANCE FLUID PF-5052", "3M NOVEC 7100 ENGINEERED FLUID" and "3M NOVEC 7000 ENGINEERED FLUID" available from 3M Co., St. Paul, Minn.

In one embodiment, the resulting fluorinated compounds can be purified to isolate the desired dioxolane-containing hydrofluoro ether. Purification can be done by conventional means including distillation, absorption, extraction, chromatography and recrystallization. The purification can be done to isolate the compound of the present disclosure (in all of its stereoisomeric forms) from impurities, such as starting materials, byproducts, etc. The term "purified form" as used herein means the compound of the present disclosure is at least 95, 98, 99%, or even 99.9 wt % pure.

The compounds of the present disclosure may be used as a working fluid in a variety of applications. The working fluids may include at least 5%, 10%, 15%, 20%, 25%, 50%, 70%, 80%, 90%, 95%, 99%, or even 100% by weight of the above-described formula (I) compounds based on the total weight of the working fluid. In addition to the compounds of the present disclosure, the working fluids may include a total of up to 95%, 90%, 85%, 80%, 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, unsaturated hydrochlorocarbons, unsaturated hydrochlorofluorocarbons, unsaturated hydrofluorocarbons, non-hetero atom-containing hydrofluoroolefins, hydrochloroolefins, hydrochlorofluoroolefins, unsaturated hydrofluoroethers, or mixtures thereof, based on the total weight of the working fluid. Such additional components can be chosen to modify or enhance the properties of a composition for a particular use.

In one embodiment, the working fluid has no flash point (as measured, for example, following ASTM D-3278-96 e-1).

In one embodiment, the compound of the present disclosure may be used in an apparatus for heat transfer that includes a device and a mechanism for transferring heat to or from the device.

The mechanism for transferring heat may include a heat transfer working fluid that includes a compound of formula (I) of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath. In some systems, such as etchers, ashers, PECVD chambers, vapor phase soldering devices, and thermal shock testers, the upper desired operating temperature may be as high as 170° C., as high as 200° C., as high as 250° C. or even higher.

In some embodiments, the compounds of the present disclosure may be used as a heat transfer agent for use in vapor phase soldering. In using the compounds of the present disclosure in vapor phase soldering, the process described in, for example, U.S. Pat. No. 5,104,034 (Hansen) can be used, which description is hereby incorporated by reference. Briefly, such process includes immersing a component to be soldered in a body of vapor comprising at least a dioxolane-containing compound of the present disclosure to melt the solder, hi carrying out such a process, a liquid pool of the dioxolane-containing compound (or working fluid that includes the dioxolane-containing compound) is heated to boiling in a tank to form a saturated vapor in the space between the boiling liquid and a condensing means, A workpiece to be soldered is immersed in the vapor (at a temperature of greater than 170° C., greater than 200° C., greater than 230° C., 250C, or even greater), whereby the vapor is condensed on the surface of the workpiece so as to melt and reflow the solder. Finally, the soldered workpiece is then removed from the space containing the vapor.

In another embodiment, the compound of the present disclosure is used in an apparatus for converting thermal energy into mechanical energy in a Rankine cycle. The apparatus may include a working fluid that includes one or more compounds of formula (I). The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more compounds of formula (I) to form a vaporized working fluid. In some embodiments, the heat is transferred from the heat source to the working fluid in an evaporator or boiler. The vaporized working fluid may be pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

in one embodiment, the compound of the present disclosure is used in a cleaning composition along with one or more co-solvents. In some embodiments, the present disclosure relates to a process for cleaning a substrate. The cleaning process can be carried out by contacting a contaminated substrate with a cleaning composition. The compound of the present disclosure can be utilized alone or in admixture with each other or with other commonly-used cleaning co-solvents. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof. Such co-solvents can be chosen to modify or enhance the solvency properties of a cleaning composition for a particular use and can be utilized in ratios (of co-solvent to compounds according to formula (I)) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more compounds of the present disclosure and optionally one or more surfactants. Suitable surfactants include those surfactants that are sufficiently soluble in the compound of the present disclosure, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In still another embodiment, the compound of the present disclosure is used in a dielectric fluids, which can be used in electrical devices (e.g., capacitors, switchgear, transformers, or electric cables or buses). For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more compounds of formula (I) and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application comprising the compounds of formula (I) are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In another embodiment, the present disclosure relates to coating compositions comprising (a) a solvent composition that includes one or more compounds of the present disclosure, and (b) one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include unsaturated perfluoropolyether, unsaturated hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, unsaturated perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the compounds of formula (I) function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the compounds of formula (I); and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the compound(s) of formula (I), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure further relates to electrolyte compositions that include one or more compounds of the present disclosure. The electrolyte compositions may comprise (a) a solvent composition including one or more of the compounds according to formula (I); and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, $PF_6^-$ anion or a bis (perfluoroalkanesulfonyl)imide anion); that are at least partially soluble in a selected compound of formula (I) (or in a blend thereof with one or more other compounds of formula (I) or one or more conventional electrolyte solvents); and that at least partially dissociate to form a conductive electrolyte composition. The salts may be stable over a range of operating voltages, are non-corrosive, and may be thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, (perfluoroalkanesulfonypimides, bis(perfluoroalkanesulfonyl)methides, and tris(perfluoroalkanesulfonyl) methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis (perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated. The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis (fluorosulfonyl)imide (Li-FSI), and mixtures of two or more thereof.

The electrolyte compositions of the present disclosure can be prepared by combining at least one electrolyte salt and a solvent composition including at least one compound of formula (I), such that the salt is at least partially dissolved in the solvent composition at the desired operating temperature. The compounds of the present disclosure (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the compound(s) of formula (I) (for example, such that the compound(s) of formula (I) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1,3-dioxolane, alkyl-substituted 1,3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads); $Li_{4/3}Ti_{5/3}O_4$ the lithium alloy compositions described in U.S. Pat. No. 6,203,944 (Turner et al.) and U.S. Pat. No. 6,255,017 (Turner); and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e.g., carbon black for negative electrodes and carbon black, flake graphite and the like for positive electrodes.

The electrochemical devices of the present disclosure can be used in various electronic articles such as computers, power tools, automobiles, telecommunication devices, and the like.

Exemplary embodiments of the present disclosure, include, but are not limited to the following:

Embodiment 1

A dioxolane-containing compound of formula (I)

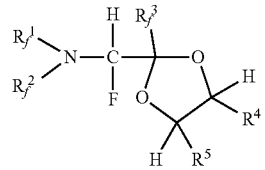

wherein (i) $R_f^1$ and $R_f^2$ are independently linear or branched perfluoroalkyl groups having with 1-8 carbon atoms and optionally comprise at least one catenated heteroatom, or (ii) $R_f^1$ and $R_f^2$ are bonded together to form a ring structure having 4-6 carbon atoms and optionally comprise one or more catenated heteroatoms;
$R_f^3$ is a linear or branched perfluoroalkyl groups having with 1-3 carbon atoms; and
$R^4$ and $R^5$ are independently selected from H, F, Cl, a linear or branched alkyl group having 1-3 carbon atoms, optionally wherein the alkyl group comprises at least one of: fluorine, chlorine, a hydroxyl group, or a catenated heteroatom.

Embodiment 2

The dioxolane-containing compound of embodiment 1, wherein $R^4$ and $R^5$ are H.

Embodiment 3

The dioxolane-containing compound of any one of the previous embodiments, wherein $R_f^3$ is $CF_3$.

Embodiment 4

The dioxolane-containing compound of any one of the previous embodiments, wherein $R_f^1$ and $R_f^2$ are bonded together to form a 5, 6, or 7 membered ring.

Embodiment 5

The dioxolane-containing compound of any one of the previous embodiments, wherein $R_f^1$ and $R_f^3$ are bonded together to form a 6-membered perfluorinated ring comprising a catenated O atom.

Embodiment 6

The dioxolane-containing compound of embodiment 5, wherein $R_f^1$ and $R_f^2$ form a morpholine group.

Embodiment 7

The dioxolane-containing compound of any one embodiments 1-4, wherein $R_f^1$ and $R_f^2$ are bonded together to form a 6-membered perfluorinated ring comprising an additional catenated N atom.

Embodiment 8

The dioxolane-containing compound of embodiment 7, wherein $R_f^1$ and $R_f^2$ form an N-perfluoroalkyl piperizine group.

Embodiment 9

The dioxolane-containing compound of any one of embodiments 1-4, wherein $R_f^1$ and $R_f^2$ form a pyrrolidine group.

Embodiment 10

The dioxolane-containing compound of any one of embodiments 1-3, wherein $R_f^1$ and $R_f^2$ are independently selected from $CF_3$, $C_2F_5$, and $C_3F_7$.

Embodiment 11

The dioxolane-containing compound of any one of the previous embodiments, wherein the dioxolane-containing compound is nonflammable based on closed-cup flashpoint testing following ASTM D-327-96 e-1.

Embodiment 12

The dioxolane-containing compound of any one of the previous embodiments, wherein the dioxolane-containing compound has a global warming potential of less than 100.

Embodiment 13

A composition comprising a purified form of the dioxolane-containing compound according to any one of the previous embodiments.

Embodiment 14

A working fluid comprising the dioxolane-containing compound according to any one of embodiments 1-11, wherein the dioxolane-containing compound is present in the working fluid in an amount of at least 5% by weight based on the total weight of the working fluid.

Embodiment 15

The working fluid of embodiment 14, wherein the working fluid further comprises a co-solvent.

Embodiment 16

Use of the dioxolane-containing compound of any one embodiments 1-11, wherein the dioxolane-containing compound is in a cleaning composition.

Embodiment 17

Use of the dioxolane-containing compound of any one embodiments 1-11, wherein the dioxolane-containing compound is an electrolyte solvent or additive.

Embodiment 18

Use of the dioxolane-containing compound of any one embodiments 1-11, wherein the dioxolane-containing compound is a heat transfer fluid.

Embodiment 19

Use of the dioxolane-containing compound of any one embodiments 1-11, wherein the dioxolane-containing compound is a vapor phase soldering fluid.

Embodiment 20

An apparatus for heat transfer comprising:
a device; and
a mechanism for transferring heat to or from the device, the mechanism comprising a heat transfer fluid that comprises the dioxolane-containing compound according to any one of embodiments 1-11.

Embodiment 21

An apparatus for heat transfer according to embodiment 20, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 22

An apparatus according to any one of embodiments 20-21, wherein the mechanism for transferring heat is a component in a system for maintaining a temperature or temperature range of an electronic device.

Embodiment 23

An apparatus according to any one of embodiments 20-21, wherein the device comprises an electronic component to be soldered.

Embodiment 24

A method of transferring heat comprising:
providing a device; and
transferring heat to or from the device using a heat transfer fluid that comprises a dioxolane-containing compound according to any one of embodiments 1-11.

Embodiment 25

A method of making the dioxolane-containing hydrofluoroether, the method comprising:
(a) contacting a 1,2-diol compound with a fluorinated ethylenically unsaturated compound in the presence of a base, the fluorinated ethylenically unsaturated compound comprising (i) an internal double bond, (ii) an olefinic C—F bond, and (iii) a fluorine atom alpha to the internal double bond.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: phr=parts per hundred rubber; g=grams, min=minutes, h=hour, ° C.=degrees Celsius, MPa=megapascals, and N-m=Newton-meter.

Example 1: Preparation of

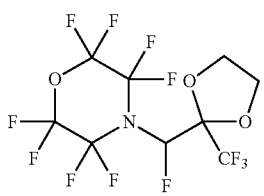 [SMILES: FC(N1C(F)(F)C(F)(F)OC(F)(F)C1(F)F)C1(C(F)(F)F)OCCO1]

Ethylene glycol (36 g, 5.81.62 mmol, 1.5 equiv.), potassium hydroxide (43.51 g, 775.49 mmol, 2 equiv.), and acetonitrile (140 g) were added to a stainless steel Parr reactor (obtained from Parr Instrument Company, Moline Ill.). The apparatus was sealed and cooled to −78° C. The reactor was evacuated and 2,2,3,3,5,5,6,6-octafluoro-4-(perfluoroprop-1-en-1-yl)morpholine (140 g, 387.74 mmol, 1 equiv.) was vacuum transferred to the apparatus. The vessel was fully sealed and allowed to reach room temperature and was subsequently heated to 80° C. for 72 h. The reactor was then cooled and vented. The contents were poured into a 1 L beaker containing ice water. The fluorochemical phase was collected and the water layer was washed (3×, 100 mL each time) with a fully-fluorinated liquid (available under the trade designation "3M PERFORMANCE LIQUID PF-5052", from 3M Co., St. Paul, Minn.). The fluorochemical phases were collected and the material was purified via fractional distillation to afford 2,2,3,3,5,5,6,6-octafluoro-4-(fluoro(2-(trifluoromethyl)-1,3-dioxolan-2-yl)methyl)morpholine as a clear, colorless liquid.

Example 2: Preparation of

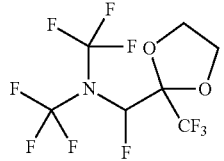 [SMILES: FC(N(C(F)(F)F)C(F)(F)F)C1(C(F)(F)F)OCCO1]

Ethylene glycol (51.1 mL, 914 mmol), potassium hydroxide (126 g, 1826.6 mmol, 2.2 equiv.), and acetonitrile (117 g) were added to a stainless steel Parr reactor (obtained from Parr Instrument Company, Moline Ill.). The apparatus was sealed and cooled down to −78° C. The reactor was evacuated and 1,2,3,3,3-pentafluoro-N,N-bis(trifluoromethyl) prop-1-en-1-amine (235 g, 830.27 mmol) was vacuum transferred to the apparatus. The vessel was fully sealed and allowed to reach room temperature and was subsequently heated to 80° C. for 72 h. The reactor was then cooled and vented. The contents were poured into a 1 L beaker containing ice water. The fluorochemical phase was collected and the water layer was washed (3×, 100 mL each time) with a fully-fluorinated liquid (available under the trade designation "3M PERFORMANCE LIQUID PF-5052", from 3M Co., St. Paul, Minn.). The fluorochemical phases were collected and the material was purified via fractional distillation to afford 1,1,1-trifluoro-N-[fluoro-[2-(trifluoromethyl)-1,3-dioxolan-2-yl]methyl]-N-(trifluoromethyl)methanamine (155 g, 57% yield) as a clear, colorless liquid.

What is claimed is:

1. A dioxolane-containing compound of formula (I)

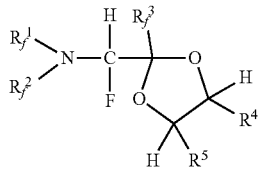

wherein (i) $R_f^1$ and $R_f^2$ are independently linear or branched perfluoroalkyl groups having with 1-8 carbon atoms and optionally comprise at least one catenated heteroatom, or (ii) $R_f^1$ and $R_f^2$ are bonded together to form a ring structure having 4-6 carbon atoms and optionally comprise one or more catenated heteroatoms;

$R_f^3$ is a linear or branched perfluoroalkyl groups having with 1-3 carbon atoms; and $R^4$ and $R^5$ are independently selected from H, F, Cl, a linear or branched alkyl group having 1-3 carbon atoms, optionally wherein the alkyl group comprises at least one of: fluorine, chlorine, a hydroxyl group, or a catenated heteroatom.

2. The dioxolane-containing compound of claim 1, wherein $R^4$ and $R^5$ are H.

3. The dioxolane-containing compound of claim 1, wherein $R_f^3$ is $CF_3$.

4. The dioxolane-containing compound of claim 1, wherein $R_f^1$ and $R_f^2$ are bonded together to form a 5, 6, or 7 membered ring.

5. The dioxolane-containing compound of claim 1, wherein $R_f^1$ and $R_f^2$ are bonded together to form a 6-membered perfluorinated ring comprising a catenated O atom.

6. The dioxolane-containing compound of claim 5, wherein $R_f^1$ and $R_f^2$ form a morpholine group.

7. The dioxolane-containing compound of claim 1, wherein $R_f^1$ and $R_f^2$ are bonded together to form a 6-membered perfluorinated ring comprising an additional catenated N atom.

8. The dioxolane-containing compound of claim 7, wherein $R_f^1$ and $R_f^2$ form an N-perfluoroalkyl piperizine group.

9. The dioxolane-containing compound of claim 1, wherein $R_f^1$ and $R_f^2$ form a pyrrolidine group.

10. The dioxolane-containing compound of claim 1, wherein $R_f^1$ and $R_f^2$ are independently selected from $CF_3$, $C_2F_5$, and $C_3F_7$.

11. A working fluid comprising the dioxolane-containing compound according to claim 1, wherein the dioxolane-containing compound is present in the working fluid in an amount of at least 5% by weight based on the total weight of the working fluid.

12. An apparatus for heat transfer comprising:
a device; and
a mechanism for transferring heat to or from the device, the mechanism comprising a heat transfer fluid that comprises the dioxolane-containing compound according to claim 1.

13. A method of transferring heat comprising:
providing a device; and
transferring heat to or from the device using a heat transfer fluid that comprises a dioxolane-containing compound according to claim 1.

14. A composition comprising a purified form of the dioxolane-containing compound according to claim 1.

15. The dioxolane-containing compound of claim 1, wherein the dioxolane-containing compound is nonflammable based on closed-cup flashpoint testing following ASTM D-327-96 e-1.

16. The dioxolane-containing compound of claim 1, wherein the dioxolane-containing compound has a global warming potential of less than 100.

17. The working fluid of claim 11, wherein the working fluid further comprises a co-solvent.

18. An apparatus according to claim 12, wherein the mechanism for transferring heat is a component in a system for maintaining a temperature or temperature range of an electronic device.

\* \* \* \* \*

UNITED STATES PATENT AND TRADEMARK OFFICE
CERTIFICATE OF CORRECTION

PATENT NO. : 10,934,281 B2
APPLICATION NO. : 16/323282
DATED : March 2, 2021
INVENTOR(S) : Georgiy Teverovskiy It is certified that error appears in the above-identified patent and that said Letters Patent is hereby corrected as shown below:

On the Title Page

Column 2,
Under Item (56) "Other Publications", Line 8, delete "jounal" and insert -- journal --, therefor.
Under Item (56) "Other Publications", Line 9, delete ""Reacion" and insert -- "Reaction --, therefor.
Under "Abstract", Line 2, delete "(I)" and insert -- (I): --, therefor.
Under "Abstract", Line 3, delete "perfluoroalkyi" and insert -- perfluoroalkyl --, therefor.
Under "Abstract", Line 8, delete "perfluoroalkyi" and insert -- perfluoroalkyl --, therefor.

In the Specification

Column 1,
Line 61, delete "above," and insert -- above. --, therefor.

Column 9,
Line 28, delete "solder, hi" and insert -- solder. In --, therefor.
Line 32, delete "means," and insert -- means. --, therefor.

Column 10,
Line 14, delete "though" and insert -- through --, therefor.
Line 58, delete "in" and insert -- In --, therefor.

Column 14,
Line 35, delete "haloalkylsubstituted" and insert -- haloalkyl substituted --, therefor.
Line 39, delete "(perfluoroalkanesulfonypimides," and insert -- (perfluoroalkanesulfonyl)imides, --, therefor.

Column 16,
Line 47, delete "$R_f^3$" and insert -- $R_f^2$ --, therefor.
Line 66, delete "piperizine" and insert -- piperazine --, therefor.

Signed and Sealed this
Tenth Day of May, 2022

*Katherine Kelly Vidal*
Katherine Kelly Vidal
*Director of the United States Patent and Trademark Office*